United States Patent
Liu

(12) 
(10) Patent No.: US 6,533,914 B1
(45) Date of Patent: *Mar. 18, 2003

(54) MICROFABRICATED INJECTOR AND CAPILLARY ARRAY ASSEMBLY FOR HIGH-RESOLUTION AND HIGH THROUGHPUT SEPARATION

(76) Inventor: Shaorong Liu, 303 Ridgeview Dr., Tracey, CA (US) 95376

( * ) Notice: Subject to any disclaimer, the term of this patent is extended or adjusted under 35 U.S.C. 154(b) by 161 days.

This patent is subject to a terminal disclaimer.

(21) Appl. No.: 09/604,861

(22) Filed: Jun. 27, 2000

Related U.S. Application Data

(60) Provisional application No. 60/142,735, filed on Jul. 8, 1999.

(51) Int. Cl.[7] .............................. C02F 1/40; C02F 11/00; C25B 11/00; C25B 13/00; C25B 9/00; G01N 27/27; G01N 27/403; G01N 27/453
(52) U.S. Cl. ..................... 204/601; 204/600; 204/603; 204/451; 204/452
(58) Field of Search ................................ 204/600, 601, 204/451, 452, 603

(56) References Cited

U.S. PATENT DOCUMENTS

| | | | | |
|---|---|---|---|---|
| 5,296,375 A | | 3/1994 | Kricka et al. ................ | 435/291 |
| 5,304,487 A | | 4/1994 | Wilding et al. ............. | 435/291 |
| 5,483,075 A | | 1/1996 | Smith et al. ............. | 250/458.1 |
| 5,560,811 A | * | 10/1996 | Briggs et al. ................ | 204/451 |
| 5,599,503 A | | 2/1997 | Manz et al. ............. | 422/82.05 |
| 5,644,395 A | * | 7/1997 | Folta ....................... | 356/244 |
| 5,795,788 A | | 8/1998 | Bevan et al. ................ | 436/161 |
| 5,856,174 A | | 1/1999 | Lipshutz et al. ......... | 435/286.5 |
| 5,872,010 A | * | 2/1999 | Karger et al. ................ | 204/451 |
| 5,890,745 A | | 4/1999 | Kovacs ........................ | 285/24 |
| 5,904,824 A | | 5/1999 | Oh .............................. | 204/601 |
| 5,906,723 A | | 5/1999 | Mathies et al. ............. | 204/603 |
| 5,958,203 A | | 9/1999 | Wallace et al. ............. | 204/451 |
| 5,972,187 A | * | 10/1999 | Parce et al. ................. | 204/450 |
| 5,976,336 A | | 11/1999 | Dubrow et al. ............. | 204/453 |
| 6,001,229 A | | 12/1999 | Ramsey et al. ............. | 204/451 |
| 6,042,709 A | | 3/2000 | Parce et al. ................. | 204/453 |
| 6,046,056 A | | 4/2000 | Parce et al. ................. | 436/514 |
| 6,054,034 A | | 4/2000 | Soane et al. ................ | 204/601 |
| 6,103,199 A | * | 8/2000 | Bjornson et al. ........... | 204/450 |
| 6,110,332 A | * | 8/2000 | Swierkowski ............... | 204/242 |
| 6,149,787 A | * | 11/2000 | Chow et al. ................ | 204/451 |
| 6,270,644 B1 | * | 8/2001 | Mathies et al. ............. | 204/600 |
| 6,319,476 B1 | * | 11/2001 | Victor et al. ............. | 210/198.2 |

OTHER PUBLICATIONS

Culbertson, Christopher T. et al., "Dispersion Sources for Compact Geometries on Microchips", *Anal. Chem.*, 70:3781–3789, 1998.

(List continued on next page.)

*Primary Examiner*—Jill Warden
*Assistant Examiner*—Jennine Brown
(74) *Attorney, Agent, or Firm*—Richard A. Nakashima; Blakely, Sokoloff, Taylor & Zafman

(57) ABSTRACT

The present invention concerns methods and apparatus for the high resolution, high output electrophoretic separation of molecules. In preferred embodiments, the methods and apparatus are of use for DNA sequencing. The apparatus comprises a hybrid device, comprising a microfabricated chip injector attached to an array of one or more capillaries. The chip injector is designed with incorporation and injector channels that precisely match the capillaries, to minimize or eliminate dead volume in the system. DNA sequencing runs of over 700 bases, with a run time of less than one hour, may be accomplished with the methods and apparatus disclosed herein.

22 Claims, 11 Drawing Sheets

OTHER PUBLICATIONS

Liu, Shaorong et al., "Optimization of High–Speed DNA Sequencing on Microfabricated Capillary Electrophoresis Channels", *Anal. Chem.*, 71:566–573, 1999.

Salas–Solano et al., "A Sample Purification Method for Rugged and High–Performance DNA Sequencing by Capillary Electrophoresis Using Replaceable Polymer Solutions. B. Quantitative Determination of the Role of Sample Matrix Components of Sequencing Analysis", *Anal. Chem.*, 70:1528–1535, 1998a.

Salas–Solano et al., "Routine DNA Sequencing of 1000 Bases in Less Than One Hour by Capillary Electrophoresis with Replaceable Linear Polyacrylamide Solutions", *Anal. Chem.*, 70:3996–4003, 1998b.

Schmalzing et al., "DNA Sequencing On Microfabricated Electrophoretic devices", *Anal. Chem.*, 70:2303–2310, 1998.

Simpson et al., "High Throughput Genetic Analysis Using Microfabricated 96–Sample Capillary Array Electrophoresis Microplates", *Proc. Natl. Acad. Sci., USA*, 95:2256–2261, 1998.

Wooley et al., "Ultra–High–Speed DNA Sequencing Using Capillary Electrophoresis Chips", *Anal. Chem.*, 67:3676–3680, 1995.

Wooley and Mathies, "High–Speed DNA Genotyping Using Microfabricaed Capillary Array Electrophoresis Chips", *Anal. Chem.*, 69:2181–2186, 1997.

Karger, Barry L. et al., Copy of U.S. Patent Specification filed Sep. 2, 1997, entitled "Microfabricated Hybrid Capillary Array and Multichannel Detection Assembly", now abandoned.

Best et al., "Separation of Fragments up to 570 Bases in Length by Use of 6–Percent T Non–Cross–Linked Polyacrylamide for DNA Sequencing in Capillary Electrophoresis", *Anal. Chem.*, 66:4063–7, 1994.

Cohen et al., "Separation and Analysis of DNA Sequence Reaction Products by Capillary Gel Electrohoresis", *J. Chromatog.* 516:49–60, 1990.

Drossman et al., "High–Speed Separations of DNA Sequencing Reactions by Capillary Electrophoresis", *Anal. Chem.*, 62:900–3, 1990.

Effenhauser et al., "High–Speed Separation of Antisense Oligounucleotides on a Micromachined Capillary Electrophoresis Device", *Anal. Chem.*, 66:2949–2953, 1994.

Friedman, N.A. and Meldrum, D.R., "Capillary Tube Resistive Thermal Cycling", *Anal. Chem.* 70:2997–3002, 1998.

Giddings et al., "A Software System for Data Analysis in Automated DNA Sequencing", *Genome Research*, 8:644–65, 1998.

Huang et al., "Capillary Array Electrophoresis Using Laser–Excited Confocal Fluorescence Detection", *Anal. Chem.*, 64:967–72, 1992a.

Huang et al., "DNA Sequencing Using Capillary Array Electrophoresis", *Anal. Chem.* 64:2149–54, 1992b.

Jacobson et al., "Effects of Injection Schemes and Column Geometry on the Performance of Microchip Electrophoresis Devices", *Anal. Chem.*, 66:1107–1113, 1994.

Luckey et al., "High Speed DNA Sequencing by Capillary Electrophoresis", *Nucl. Acids Res.*, 18:4417–21, 1990.

Mathies, R.A. and Huang, X.C. "Capillary Array Electrophoresis: An Approach to High–Speed, High–throughput DNA Sequencing", *Nature (London)* 359:167–9, 1992.

Mathies et al., "Laser–Excited COnfocal Fluorescence Gel Scanner", *Reviews of Scientific Instruments*, 65:807–12, 1994.

Mathies et al., "Microfabricated Capillary Array Electrophoresis Systems for High–Performance DNA Sequencing and Genotyping". HPCE '99 Final Program p41, 1999, Palm Springs, CA (Abstract Only).

Müller et al., "Ultrafast DNA analysis by capillary electrophoresis/laser–induced fluorescence detection", *Electrophoresis*, 19:1436–44, 1998.

Ruiz–Martinez et al., "DNA Sequencing by Capillary Electrophoresis With Replaceable Linear Polyacrylamide and Laser–Induced Fluorescence Detection", *Anal. Chem.* 65:2851–8, 1993.

Salas–Solano et al., "A. Sample Purification Method for Rugged and High–Performance DNA Sequencing by Capillary Electrophoresis Using Replaceable Polymer Solutions. B. Quantitative Determination of the Role of Sample Matrix Components on Sequencing Analysis", *Anal. Chem.*, 70:1528–1535, 1998.

Swerdlow et al., "Three DNA Sequencing Methods Using Capillary Gel Electrophoresis and Laser–Induced Fluorescence", *Anal. Chem.*, 63:2835–41, 1991.

Takahashi et al., "Multiple Sheath–flow Gel Capillary Array Electrophoresis for Multicolor Fluorescent DNA Detection", *Anal. Chem.*, 66(7):1021–6, 1994.

Tan and Yeung, "Automation and Integration of Multiplexed On–Line Sample Preparatin With Capillary Elctrophoresis for High–Throughput DNA Sequencing", *Anal. Chem.*, 70:4044–53, 1998.

Ueno and Yeung, "Simultaneous Monitoring of DNA Fragments Separated by Electrophoresis in a Multiplexed Array of 100 Capillaries", *Anal. Chem.*, 66:1424–31, 1994.

Voss et al., "The use of capillary electrophoresis to study methylation patterns in DNA", *The International Society for Optical Engineering–SPIE*. vol. 2680, Feb. 4–10, San Jose, CA, 1995.

Wooley an Mathies, "Ultra–high–speed DNA fragment separations using microfabricated capillary array electrophoresis chips", *Proc. Natl. Acad. Sci., USA*, 91:11348–11352, 1994.

* cited by examiner (a) Channel of rough boundaries (b) Channel of a flat profile (section view)

Poor alignment

MICROFABRICATED INJECTOR AND CAPILLARY ARRAY ASSEMBLY FOR HIGH-RESOLUTION AND HIGH THROUGHPUT SEPARATION

This patent application claims the benefit under 35 U.S.C. §119(e) of U.S. provisional patent application Ser. No. 60/142,735, filed July 8, 1999.

BACKGROUND OF THE INVENTION

1. Field of the Invention

The present invention concerns the field of high throughput assays of molecules. More particularly, the present invention concerns methods and apparatus of use in DNA sequencing and other high throughput assays, using a novel hybrid apparatus comprising an array of capillaries attached to a microfabricated chip injector.

2. Description of Related Art

DNA sequencing chemistry was first developed by Sanger et al. (1977) and by Maxam and Gilbert (1977). Sanger's dideoxy chain termination method is the most widely used for high-volume sequencing, due to the development of automated fluorescence sequencing based on labeled primers or terminators (Smith et al., 1986; Prober et al., 1987; Tabor et al., 1990; Ansorge et al., 1987). Implementation of this technology has produced automated slab-gel-based sequencers with 1–2 kb/hr capacity (Hunkapiller et al., 1991). This capacity may be pushed to 5 kb/hr through incremental improvement by increasing the number of lanes, decreasing the gel thickness, and improving the labeling chemistry and the detection capabilities. Such improvements will plateau unless revolutionary technique(s) are invented and applied. Generally, the slab gel format is not easily adapted for automated sample loading and it is probably incompatible with further efforts to miniaturize the sequencing process.

A number of advances have been made in DNA sequencing technology since 1990. These originate from two developments. First, by reducing the cross section of the gel cavity, higher electric fields can be applied without producing gel-heating anomalies, thereby providing faster separations. Second, laser-excited fluorescence detection is so sensitive that smaller separation lanes can be easily detected.

A number of workers have explored the use of capillary gel electrophoresis (CGE) for the rapid separation of DNA extension fragments in one-color and eventually 4-color detection formats (Drossman et al., 1990; Luckey et al., 1990; Swerdlow et al., 1991; Cohen et al., 1990; Ruiz-Martinez et al., 1993; Best et al., 1994). Capillary electrophoresis (CE) separations of DNA sequencing fragments are about 10 times faster than slab gels and are often complete in under 2 hr. However, the throughput of CE-based DNA sequencing has been limited by the lack of a method for running multiple capillaries (lanes) in parallel.

Mathies and coworkers (Huang et al., 1992a, 1992b; Mathies et al., 1992) developed a solution to this limitation by using a laser-excited confocal fluorescence scanner (Mathies et al., 1994) to interrogate bundled capillaries. The capillaries were translated past the focused laser beam and sequentially sampled. The capillaries separated at the injection end of the array to facilitate rapid sample loading from a microtitre dish array.

Several different groups have developed alternative capillary array apparatus. Kambara and coworkers (Takahashi et al., 1994) developed a capillary array system based on sheath flow detection scheme. Two different laser excitation beams were passed through the sheath flow and the fluorescence was imaged to a CCD for multicolor detection. This format has the advantage that all lanes are continuously excited and the flow cell has good optical quality with low scattering noise. Disadvantages of this arrangement include the complexity of the sheath flow cell and extra band-broadening due to the electric field distortion in the flow cell. A conceptually similar system was described by Dovichi et al. (1995). Ueno and Yeung (1994) developed a capillary array system where the laser is line-focused on a stationary array and the resulting fluorescence is imaged to a CCD for detection. A two-color-ratio method was used for DNA sequencing. Two 96-capillary-array DNA sequencers have been successfully developed and are currently used. One is based on Mathies' confocal detection design and the other is based on Kambara's sheath flow arrangement.

Research efforts have also been given to sequencing with short separation channels on microfabricated CE chips (Woolley et al., 1995; Schmalzing et al., 1998; Liu et al., 1999) or short capillaries (Muller et al., 1998) to increase the separation speed. Woolley and Mathies (1995) performed high-speed separations of DNA sequencing fragments on microfabricated CE chips. DNA separations were achieved in 50 $\mu$m×8 $\mu$m×3.5 cm channels microfabricated in a 2-in.×3 in. glass sandwich structure. Approximately 150 bases of four-color sequencing mixture were separated in 9 min and base-assigned with an accuracy of 97%. Single-base resolution was obtained out to 200 bases for both the one- and four-color separations. Alternative methods for detection of separated molecules on CE chips have been disclosed (U.S. Pat. No. 5,906,723, incorporated herein by reference in its entirety.)

Theoretically, high-speed separation should be achieved on capillaries provided they are short. Muller et al. (1998) have experimentally demonstrated this using a 7-cm-long (50-$\mu$m-i.d.) capillary and one-color sequencing mixture. Single base resolution was observed up to 300 bases in 3 min. However, it is difficult to arrange 96 or more such capillaries to carry out sample injection and separation for high-throughput DNA sequencing. Recently, Schmalzing, et al (1998) performed a separation of one-color sequencing mixture using an 11.5-cm-long microfabricated channel. Single-base resolution was obtained up to ~400 bases in 14 min. Liu et al. (1999) have demonstrated high-speed DNA sequencing on a 7 cm-long microfabricated channel. Single-base resolution of reached 500 bases in 9.2 min using a one-color sequencing mixture, and four-color sequencing exhibited a base-calling accuracy of 99.4% up to 500 bases.

Current efforts on the development of high-speed and high-throughput DNA sequencing are in two major areas, conventional CGE and microfabricated electrophoresis chips. Research with conventional CGE focuses on improving the sieving matrix and separation conditions, and increasing the number of capillaries. Research on microfabricated electrophoresis chips is more exploratory. In order to achieve high-speed and high-throughput analysis, Mathies et al. (1999) developed a radial chip. This chip has a common anode reservoir in the center of a circular 10 cm diameter wafer and an array of 96 channels extending outward toward injector units at the perimeter of the wafer. A rotary scanning detection system consists of a rotating objective head coupled to a four-color confocal detection unit. High-speed and high-throughput assays have been demonstrated on this radial chip for genotyping. High quality sequencing has not been obtained due to the limited effective separation distance.

Other attempts are directed to the manufacture of large "chips" in order to achieve high quality sequencing separation. These approaches gain back the read-length from conventional CGE, but give up the separation speed of microfabricated CE chips. In addition, "micro" fabrication of a half-meter size chip without defects is challenging.

Sequencing separation using short separation channels (Schmalzing et al., 1998; Liu et al., 1999) improves separation speed about 10 fold compared to conventional capillaries (~40 cm). However, the sequencing read-lengths diminish by a factor of 1.5 to 2.

An unresolved need exists in the art for the development of high speed, high-throughput DNA sequencing methods and apparatus that are capable of reading DNA sequences significantly longer than 500 bases, using small amounts of DNA sample in a small sample volume. None of the methods or apparatus discussed above are capable of such separations.

SUMMARY OF THE INVENTION

The present invention solves a long-standing need in the art by providing a hybrid apparatus for high-speed, high throughput and long read length DNA sequencing separation, comprising a microfabricated chip injector attached to an array of one or more capillaries. Within the scope of the invention almost any number of capillaries may be incorporated into the apparatus, from 1, 2, 4, 8, 16, 24, 32, 48, 64, 96, 128, 160, 192, 224, 256, 288, 320, 352, 384, 416, 480, 544, 608, 672, 736, 800, 864, 928, 960 or more capillaries.

In a particularly preferred embodiment, the chip injector is configured as shown in FIG. 1. Each capillary is inserted into a connection channel. Each connection channel is connected to an injector, a cathode reservoir, a sample reservoir and a waste reservoir. Cross channels connect the sample reservoir and waste reservoir to the injector. In preferred embodiments, the inside diameter (i.d.) of the connection channel is fabricated to precisely match the outside diameter (o.d.) of the capillary, while the i.d. of the injector and cross channels is fabricated to precisely match the i.d. of the capillary. In preferred embodiments, the dead volume is less than 2 nanoliters, more preferably less than 1 nanoliter, more preferably less than 500 picoliters, more preferably less than 200 picoliters, more preferably less than 100 picoliters, more preferably less than 50 picoliters, more preferably less than 20 picoliters, more preferably less than 10 picoliters, more preferably less than 5 picoliters, more preferably less than 2 picoliters per capillary. In particularly preferred embodiments, there is no mismatch at the joint between the connection chartel and the capillary, so that there is zero dead volume in the system when the capillary is fully inserted into the connection channel.

In preferred embodiments, the hybrid apparatus is capable of performing long read-length DNA sequencing of greater than 500, more preferably 800 to 1,000, or even greater than 1,000 bases of DNA sequence in a single run. In preferred embodiments, the apparatus is high-speed (run time of less than 2 hours, more preferably less than 1 hour).

Other embodiments of the invention comprise a rotary scanner for use with the hybrid apparatus (see U.S. Pat. No. 5,483,075, incorporated herein by reference in its entirety).

In additional embodiments, the present invention comprises accessories for automated matrix filling, chip injector cleanup, sample loading and sequencing separation. Design and construction of such accessories may be accomplished by methods well known in the art. In preferred embodiments, the entire system is automated to allow rapid sample throughput with minimal human intervention needed.

In other preferred embodiments, the injector chip is designed to operate with a sample volume of 5 $\mu$l or less, more preferably of 0.5 to 2.0 $\mu$l, although sample volumes of 0.25 to 0.5 $\mu$l or even 0.1 to 0.25 $\mu$l are contemplated within the scope of the present invention.

In other embodiments, the chip injector is made of polymer materials, such as polycarbonate, poly(methyl methacrylate) (PMMA), poly(dimethylsiloxane) (PDMA), polystyrene, nitrocellulose, poly(ethylene terephthalate) (PET or Melinex), poly(tetrafluoroethylene) (teflon), etc., using laser ablation, injection molding, casting, or imprinting techniques that are well known in the art.

In certain embodiments, the present invention concerns methods of manufacture of the hybrid apparatus, comprising using a two-mask, or more preferably a three-mask procedure in combination with photolithographic etching of glass wafers to produce a hybrid array with minimal, or more preferably zero dead volume.

In additional embodiments, the present invention concerns methods of use of the hybrid apparatus, comprising using the claimed apparatus for electrophoresis of DNA sequencing products from a Sanger dideoxy reaction. The separated reaction products may be detected and analyzed by standard methods to provide DNA sequence data for long-length, high throughput and high resolution DNA sequencing.

In other embodiments, the present invention concerns methods of use of the hybrid apparatus for separations of other molecules such as peptides, proteins, polysaccharides, lipids and/or oligonucleotides using sieving matrix such as PEO, HEC, agarose, polysaccharides, polyacrylamides, and/or a mixture of those matrices.

In certain embodiments, the present invention concerns apparatus and methods of use of the hybrid device for fluidic communications. Capillaries are used to communicate, for example, between two or more chips, between a chip and an instrument, or between a sample source and a chip. The skilled artisan will realize that these examples are not intended to be limiting, but rather that the capillary array may be used to connect a first chip to any other device, including a second chip. A non-limiting example of the use of the hybrid device for communication between two chips is shown in FIG. 11. Although FIG. 11 shows connections between only two devices, it is contemplated that two, three, four or even more devices could be connected in this way through the use of capillaries. In FIG. 11, a first chip may perform one or more functions such as sample digestion and/or purification. The processed samples are then transferred via one or more capillaries to a second chip. The second chip may perform additional functions such as further sample treatment and/or separation of molecules within the samples. Another non-limiting example would be to use the capillaries to communicate between a chip and an analytical instrument, such as a UVNIS or fluorescence spectrophotometer, a liquid scintillation counter, a charge-coupled device (CCD), a gas chromatograph or a mass spectrometer (MS). Samples may be digested and/or separated on a chip and then delivered through one or more capillaries to an analytical instrument for identification as described in Zhang et al.(1999).

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Microfluidic Techniques

Figure 1:
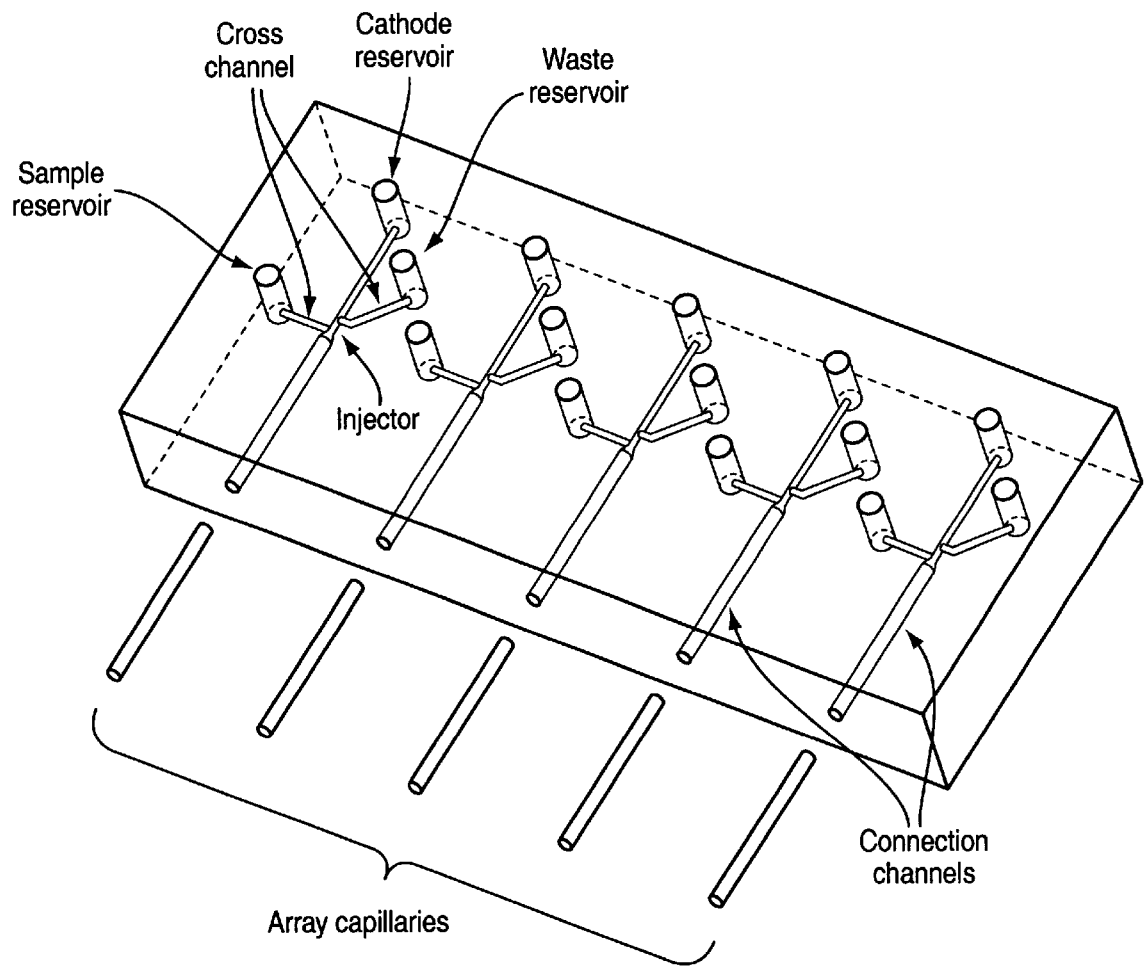
FIG. 1. A schematic diagram of a hybrid chip injector capillary array apparatus.

Microfluidic techniques include separation on a platform such as microcapillaries, designed by ACLARA Bio-Sciences Inc., or the LabChip™ liquid integrated circuits made by Caliper Technologies Inc. These microfluidic platforms require only nanoliter volumes of sample, in contrast to the microliter volumes required by other separation technologies. Miniaturizing some of the processes involved in genetic analysis has been achieved using microfluidic devices. For example, published PCT Application No. WO 94/05414, U.S. Pat. Nos. 5,304,487, 5,296,375, 5,856,174, 5,958,203, 5,976,336, 6,001,229, 6,042,709 and 6,046,056, each of which is incorporated herein by reference.

Capillary Electrophoresis

In some embodiments microcapillary arrays are contemplated to be used. Microcapillary array electrophoresis generally involves the use of a thin capillary or channel that may or may not be filled with a particular separation medium. Electrophoresis of a sample through the capillary provides a size based separation profile for the sample. The use of microcapillary electrophoresis has been reported in, e.g., Woolley and Mathies, 1994 (see also U.S. Pat. No. 6,054,034, incorporated herein by reference in its entirety). Microcapillary array electrophoresis generally provides a rapid method for size-based analysis of molecules. The high surface to volume ratio of these capillaries allows for the application of higher electric fields across the capillary without substantial thermal variation across the capillary, consequently allowing for more rapid separations. Microfabrication of microfluidic devices including microcapillary electrophoretic devices has been discussed in detail in, e.g., Jacobsen et al., 1994; Effenhauser et al., 1994; and U.S. Pat. No. 5,904,824, incorporated herein by reference. Typically, these methods comprise photolithographic etching of micron scale channels on silica, silicon or other crystalline substrates or chips, and can be readily adapted for use in the present invention. In some embodiments, the capillary arrays may be fabricated from the same polymeric materials described for the fabrication of the body of the device, using laser ablation, injection molding, casting, or imprinting techniques.

In many capillary electrophoresis methods, the capillaries are filled with an appropriate separation/sieving matrix. Typically, a variety of sieving matrices are known in the art may be used in the microcapillary arrays. Examples of such matrices include, e.g., hydroxyethyl cellulose, polyacrylamide, agarose and the like. Generally, the specific gel matrix, running buffers and running conditions are selected to maximize the separation characteristics of the particular application. For example, running buffers may include denaturants, chaotropic agents such as urea or the like, to denature nucleic acids in the sample.

Theoretical Aspects of DNA Separation Using CGE

Luckey et al. (1993) were the first to systematically investigate resolution in DNA sequencing by CGE. In their theoretical treatment, four contributions to the final bandwidth were considered: injection, diffusion, thermal gradient, and detection volume. One of the conclusions out of this model is that the dominant sources of band-broadening are injection and longitudinal diffusion. Thermal gradient and detection volume contributed, in their experiments, <2% of the total peak variances. When contributions of thermal gradient and detection volume to band-broadening are neglected and two adjacent peaks (of one base difference) are assumed equivalent, resolution (R) of these adjacent peaks can be expressed as $$R = L(\mu_1 - \mu_2) / \left\{ 4 \left( \mu_a \left[ \frac{(\mu_a E_{inj} t_{inj})^2}{12} + \frac{2DL}{\mu_a E} \right]^{1/2} \right) \right\} \quad (1)$$

where L is the separation distance, $\mu_1$ and $\mu_2$ are the mobilities of the DNA fragments of two adjacent peaks, $\mu_a$ is the average of $\mu_1$ and $\mu_2$, $E_{inj}$ and $t_{inj}$ are respectively the injection field strength and time, D is the average of the diffusion coefficients of the two fragments, and E is the separation field strength.

Figure 2:
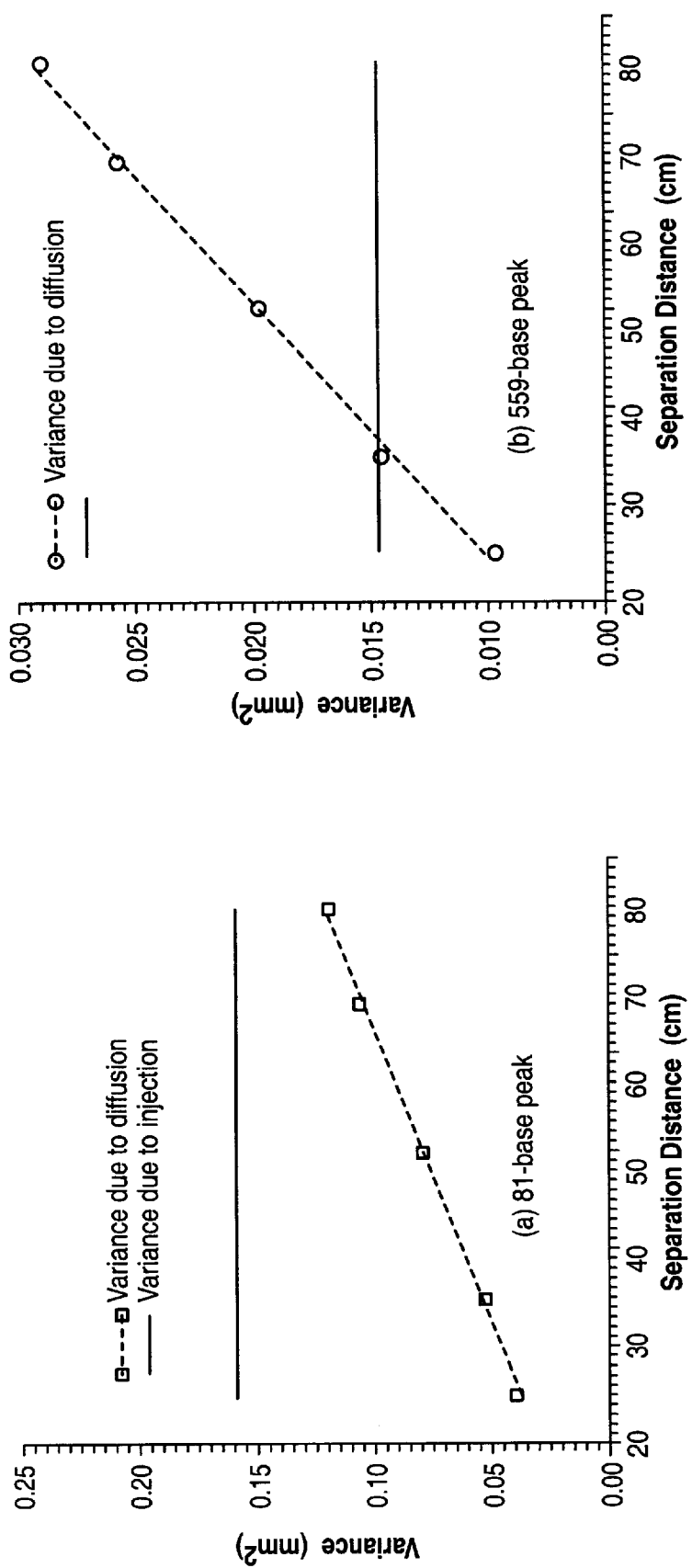
FIG. 2. Comparisons of peak variances contributed by injection and diffusion.
Figure 3:
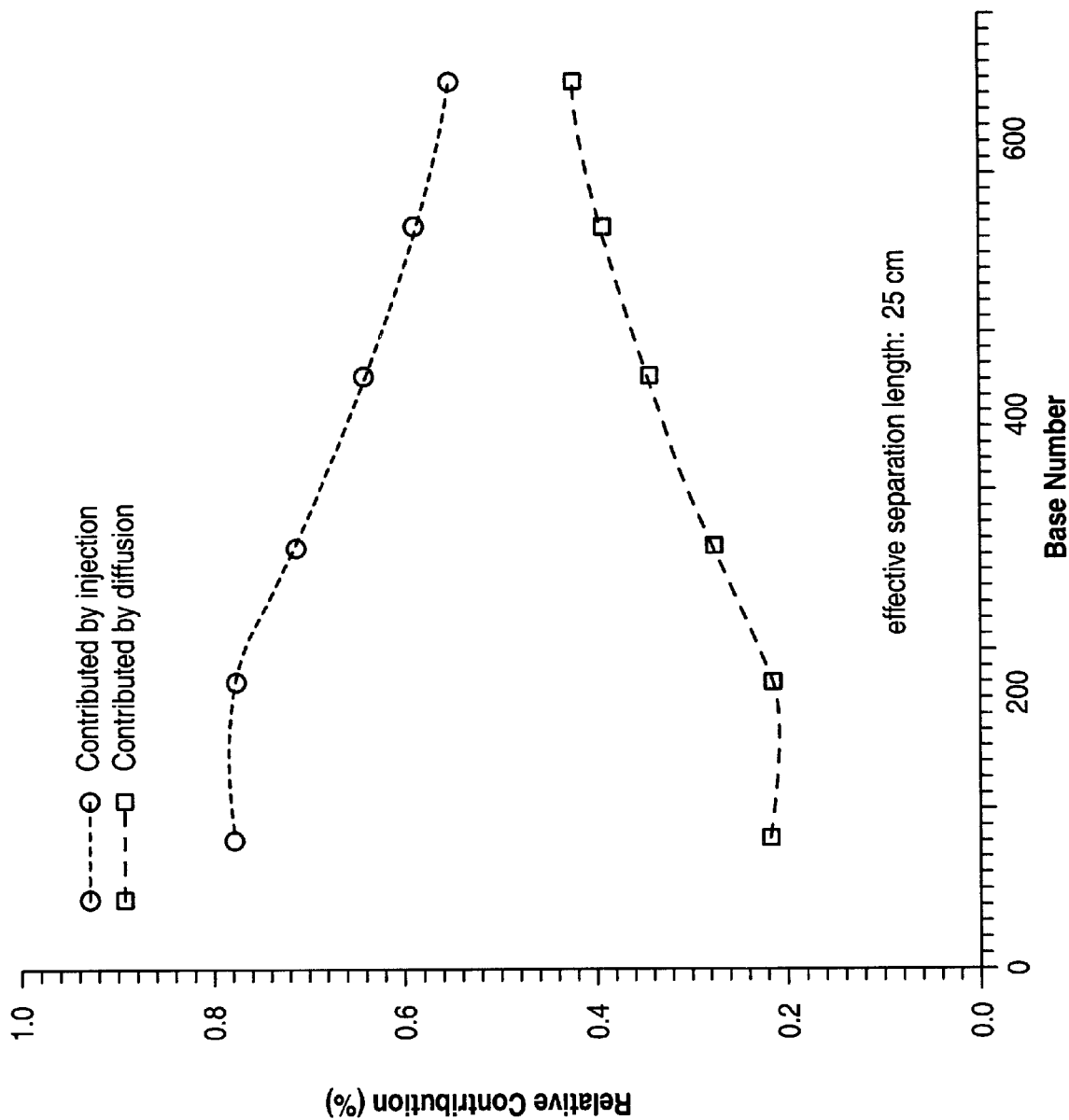
FIG. 3. Comparison of the variances contributed by injection and diffusion at an effective separation length of 25 cm.

FIG. 2 presents peak variances due to diffusion and injection as a function of separation distance using data retrieved from the reference (Luckey et al., 1993). For short fragments, sample injection is the dominant contributor to the final peak width (FIG. 2), even for an effective separation length of 75 cm which was the longest capillary Smith and coworkers ever used in their experiments (Luckey et al., 1993). For long fragments, diffusion-caused band broadening becomes more significant due to their long retention time. Sample injection is still the dominant contributor when separation distance is 37 cm or shorter (see FIG. 2). FIG. 3 represents the data of Table VII of Luckey et al. (1993). It indicates that, for an effective separation length of 25 cm, sample injection dominates the final peak width over all examined fragment lengths. Generally speaking, 25-cm separation distance is considered very long on a microfabricated CE chip.

Thus, narrowing the injection band is the most effective means to improve the separation resolution. On the other hand, the same resolution can be maintained using shortened capillaries through reducing the injection plug, with a net improvement in the separation speed.

Figure 4:
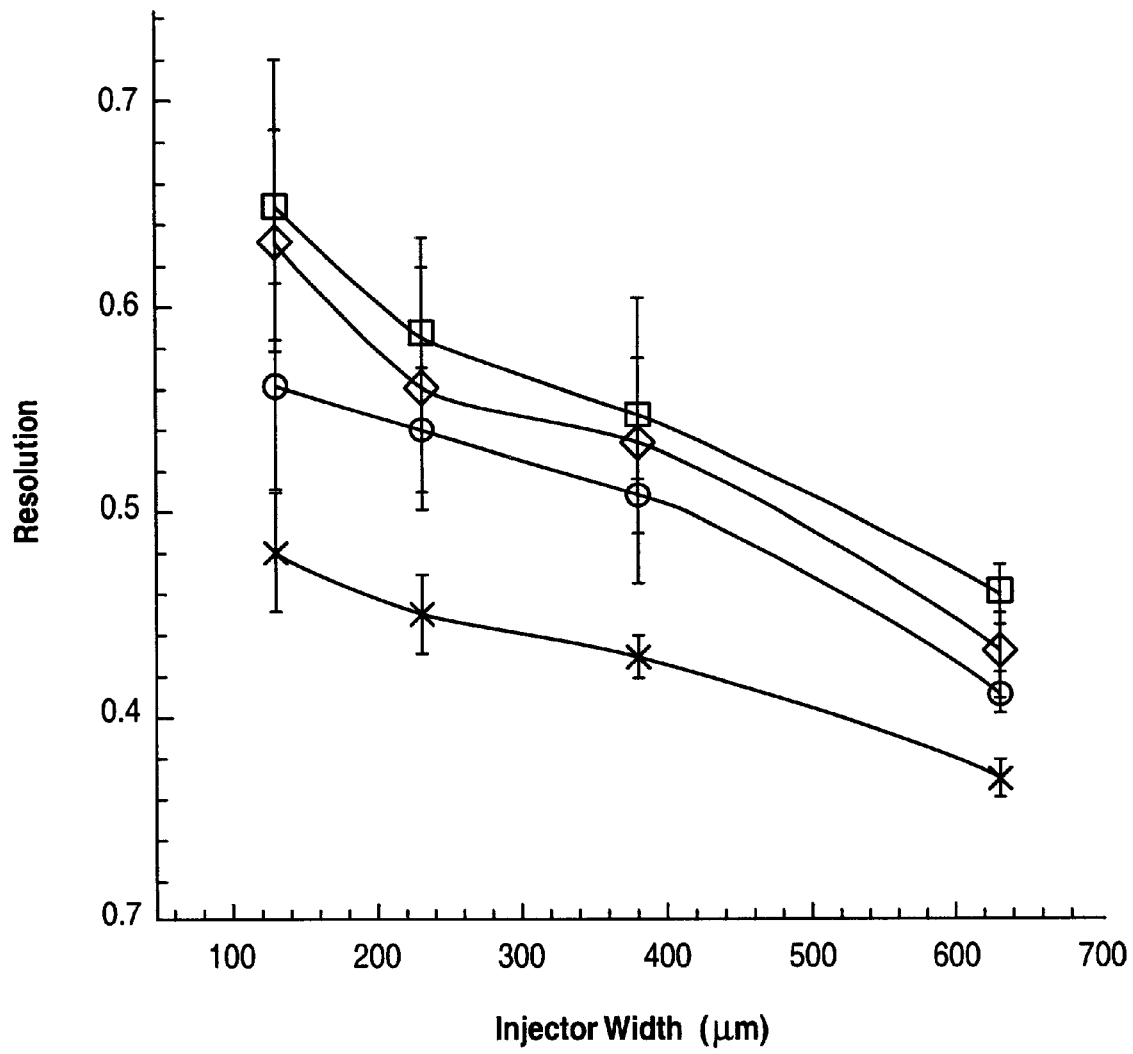
FIG. 4. Effect of injector size on resolution of DNA sequencing separations.

Fundamental chemical separation theory says that separation efficiency improves with a decrease in sample bandwidth. Liu et al. (1999) proved that this theory applies to CE chips. FIG. 4 presents resolution as a function of injector width. Small injector width yields high resolution when all other experimental conditions are kept the same.

Schmalzing et al. (1998) recently developed a similar theory for sequencing separation on CE chips, focused particularly on resolution versus separation distance. They concluded that DNA sequencing of more than 400 bases on microfabricated devices with channels of <10 cm is unlikely, assuming PAA (polyacrylamide) as the sieving matrix and a minimum resolution criterion of R (resolution)=0.5 for all bases. While increased separation distance will result in long read-length, the results provided herein as well as data in the literature (Liu et al., 1999) present better-quality results than predicted by Schmalzing et al. (1998).

In the model of Schmalzing et al. (1998), bandwidth contributed by injection was assumed to be virtually eliminated throughout the theoretical development. This might be one of the main reasons that resulted in some inaccuracy of their conclusions. The experimental data in FIG. 4 confirm the bandwidth contribution by injection.

Advantages and Disadvantages of Sequencing on CE Chips

A. Advantages

Sequencing on microfabricated electrophoresis chips has many advantages. Most of them can be attributed to the use of a chip injector. These are summarized below.

Microfabricated CE chip injectors are ideal for introduction of narrow sample plugs to a separation channel. Using pinched-injection (Jacobson et al., 1994), $\geq 100$-$\mu$m sample plugs are routinely obtained. This is about an order of magnitude lower than conventional CGE in which the sample band usually stretches to >1 mm.

Using a chip-injector, a uniform signal intensity profile is usually obtained over a wide range of fragment sizes. For sequencing using CGE, the signal intensities have an exponential profile. This profile requires a wide dynamic range for detection. For sequencing separation on chips with a cross or a twin-T injector, a uniform signal intensity profile is typically obtained (Liu et al., 1999). During injection, sample is electrophoresed through the cross channel to the injector. This electrophoresis of DNA fragments provides differential enrichment of sequencing fragments. Little change in concentration will occur at the sample/gel interface for small DNA fragments and inorganic ions because their electrophoretic mobilities are similar in free solution and in sieving matrix. On the other hand, a considerable increase in the steady-state concentration will occur at the sample/gel interface for the large fragments because of their reduced mobility in the gel. This results in a concentration compensation for large fragments. Concentrations of large fragments are always lower than those of small fragments in a typical sequencing sample. A uniform intensity profile is therefore generated.

A chip-injector requires a very small volume of sample, usually <1 $\mu$L, which is about an order of magnitude less than conventional CGE.

An extra sample cleanup is performed using a chip-injector. When sample is electrophoresed through the cross channel to the injector, at an optimized injection time, the majority of the fragments have reached a steady-state concentration in the injector while large template and enzyme molecules are still migrating in the cross channel (Liu et al., 1999). When voltages are switched to separation, only the fragments in the injector are injected into the separation channel during the separation, while DNA template and enzyme contaminants are removed from the separation channel. Removal of these large molecules has been reported essential to achieve high quality separations (Salas-Solano et al., 1998a, 1998b; Ruiz-Martinez et al., 1998). In CGE, they are removed using offline membrane filters (Ruiz-Martinez et al., 1998).

Interference of salt is minimized when a twin-T injector is used as a volumetric injector. Reduced injection efficiency is the major interference of salt for conventional CGE using electrokinetic injection. In the presence of a large amount of salt, large DNA fragments are poorly injected into the separation capillary due to the fact that electrokinetic injection is biased to small salt ions. High quality desalting is considered a key to achieve routine 1000 base sequencing separations (Salas-Solano et al., 1998a, 1998b; Ruiz-Martinez et al., 1998). This procedure may be carried out offline (labor intensive) or inline (Tan and Yeund, 1997; Swerdlow et al., 1997) (consuming large amount of DNA samples) for CGE. A twin-T injector is basically a volumetric injection device. Sample to be sequenced can be physically (through pressure, vacuum, or capillary effect) moved into the injector. All DNA fragments including salt ions in the injector are injected into the separation channel, independent of the salt concentration.

The separation capillary is straight from injection end to detection point when coupled with a CE chip injector. This arrangement helps to achieve improved resolution (especially for short separation distances) and makes it convenient to heat the separation columns.

B. Limitations of Sequencing on CE Chips

There are two major limitations for sequencing on CE chips, limited straight channel length and limited applicable real estate for reservoir arrangement.

As discussed in the Background section, increased separation distance may be necessary to further improve the read-length. The longest straight channel obtainable from a 6-inch-diameter chip is about 12–13 cm, considering multiple channels to be made on the chip and some constraints of microfabrication. Channel-folding allows longer channels to be made on a small chip. This strategy is impractical for DNA sequencing due to the degraded separation quality (Culbertson et al., 1998).

The other way to achieve long straight channels is to make large chips. The disadvantage is the fabrication cost. Current microfabrication technologies allow fabrication of chips up to 6-inch in diameter at reasonable expense. This expense increases exponentially with the chip size afterwards. A few research groups (LLNL, PE/ABD, Whitehead Institute) are developing "huge" plates to increase the channel length. A 96-channel plate has been published at the LLNL website (http://www-bio.llnl.gov/bbrp/html/balch.ab.html) with channel lengths of 48 cm. In addition to the fabrication difficulties, it is very challenging to incorporate and take advantage of 96 chip-injectors into such large chips.

The number of reservoirs that can be arranged on a multiple channel chip is limited by the reservoir size, distance between adjacent reservoirs, reservoir arrangement requirements, and applicable real estate of the chip. In order to accommodate these reservoirs, they have been spread all over the plate (Woolley et al., 1997; Simpson et al., 1998), but channels have to be curved to use these reservoirs. This arrangement works for certain separations but is not acceptable for DNA sequencing. Recently, Mathies et al. (1999) have fabricated a radial chip design for 96 channels in which all the reservoirs except for the anode one are arranged around the circumference. This area may be referred to as applicable real estate. The applicable real estate of a radial chip is maximized for reservoir arrangement. However, the longest straight channel is limited to about 6 cm out of a 6-inch-diameter chip using a radial design.

Significance of the Present Invention

One embodiment of the present invention concerns a hybrid apparatus comprising a microfabricated chip injector attached to an array of one or more regular capillaries (FIG. 1) to combine the advantages of both a chip injector and a long capillary.

Viewed from the perspective of sequencing on a chip, the hybrid device eliminates several limitations. An assembly of multiple hybrid devices represents a significant improvement to the basic radial chip design. Straight channel length and applicable real estate become virtually unlimited because capillaries of any length can be incorporated with the chip-injector and applicable real estate is a linear function of the radius of the "chip". When capillaries of 50-cm effective separation distance are incorporated with chip-injectors, the hybrid device is equivalent to a one-meter-diameter radial chip. Fabrication of such a big radial "chip" is extremely challenging if not impossible.

Seen from the perspective of sequencing using CGE, the hybrid device brings all the advantages listed associated with sequencing on chips to CGE. Separation capillaries can be shortened to increase the separation speed while maintaining the same read-length.

Using a chip injection scheme, a uniform signal intensity profile is obtained over a wide range of the number of bases. In capillary gel electrophoresis, the signal intensities have an exponential profile. This profile requires a wide dynamic range for detection. For sequencing separation on chips, a uniform signal intensity profile is typically obtained. Referring to FIG. 1, all channels are filled with sieving matrix. During injection, sample is electrophoresed through the cross channel to the injector. This electrophoresis of DNA fragments provides differential stacking of the sequencing sample. Little change in concentration will occur at the sample/gel interface for small DNA fragments and inorganic ions because their electrophoretic mobilities are similar in free solution and in sieving matrix. On the other hand, a considerable increase in the steady-state concentration will occur at the sample/gel interface for the larger fragments because of their reduced mobility in the gel. As a result, the larger the fragment, the more it gets stacked. The stacked fragments migrate to the injector with little change in concentrations. These result in an ideal compensation of the fragment concentration distribution in a typical sequencing sample where larger fragments are at a lower concentration. A uniform intensity profile is therefore generated.

Sample is electrophoresed through the cross channel to the injector during injection. At an optimized injection time, the majority of the fragments have reached a steady-state concentration in the injector while large template and enzyme molecules are still migrating in the cross channel. Only the fragments in the injector are injected into the separation channel during the separation. That is, DNA template and enzyme contaminants are removed from the separation channel.

The hybrid apparatus of the present invention thus combines the desirable features of microfabricated chip injectors with the long electrophoretic separation channels of capillary electrophoresis, providing significant advantages over either system alone.

Microfabrication Protocol

Standard photolithographic technologies well known in the art may be used for CE-chip fabrication. A non-limiting example of such a process was reported in Liu et al. (1999). Wafers used for etching and bonding were Borofloat glass wafers (Precision Glass & Optics, Santa Ana, Calif.). The waters were pre-etched in concentrated HF for 15 s and cleaned before deposition of a 1500 Angstrom amorphous silicon sacrificial layer in a plasma-enhanced chemical vapor deposition (PECVD) system (PEII-A, Technics West, San Jose, Calif.). Then, wafers were primed with hexamethyldisilazane (HMDS), spin-coated with photoresist (Shipley 1818, Marlborough, Mass.) at 5500 rpm and soft-baked at 90° C. for 20–30 min. A contact mask aligner (Quintel Corp. San Jose, Calif.) was used to expose the photoresist layer with the mask design, and the exposed photoresist was removed using a 1:1 mixture of Microposit developer concentrate (Shipley) and water. Developed waters were hard-baked at 120° C. for 10–15 min and the exposed amorphous silicon was removed using a $CF_4$ plasma in the PECVD reactor. Wafers were chemically etched with concentrated HF at room temperature (etch rate 7 $\mu$m/min) to produce channels with depths from 10 to 50 $\mu$m. The remaining photoresist was stripped using 3:1 concentrated sulfuric acid and 30% hydrogen peroxide, and the amorphous silicon was removed with a $CF_4$ plasma etch.

Access holes were drilled into the etched wafers with a 0.75 mm-diameter diamond drill bit (Crystalite, Westerville, Ohio). A finished CE ship was prepared by thermally bonding an etched and drilled plate to a flat wafer of the same size in a programmable vacuum furnace (Centurion VPM, J. M. Ney, Yucaipa, Calif.). Channels were masked to 30 $\mu$m width. The final etched channel width depended on the etch depth, ranging from 70 to 130 $\mu$m for channels from 20 to 50 $\mu$m in depth, respectively.

Preparation of Chip Injector and Electrophoresis

As disclosed by Liu et al. (1999), channel surfaces may be coated with linear polyacrylamide using minor modifications of the procedure of Hjerten (1985). Channels are first washed with 1 M NaOH for about 45 min and rinsed with water, then a solution of 0.4% (v/v) of [γ-(methacryloxy)propyl]trimethoxysilane (Sigmna, St. Louis, Mo.) and 0.2% acetic acid in acetonitrile is drawn through the channels for about 1 hour using vacuum. The channels are rinsed with acetonitrile and filled with a degassed 4% (w/v) acrylamide solution containing 0.01% (w/v) ammonium persulfate and 0.01% (v/v) N,N,N',N'-tetramethylethylenediamine (TEMED). This solution is allowed to polymerize in the channel for about 5 min, and then the channel flushed with water and dried by drawing air through the channel with vacuum.

Liu et al. (1999) further disclose that LPA may be prepared by the procedure of Carrilho et al. (1996). A 10 ml solution of 6% (w/v) acrylamide at 0° C. is purged with high-purity helium for about 1 hour. Ammonium persulfate (10 $\mu$m of 10% w/v) and 10% TEMED (10 $\mu$m of 10% v/v) are added to the acrylamide solution to initiate polymerization. After 24 h in an ice bath, urea, 10X Tris-Taps and deionized water are added to the polymerized LPA solution to produce a final LPA separation matrix containing 3 or 4% LPA, 7M urea and 1X Tris-Taps. For fragment sizing a 0.75% hydroxyethylcellulose sieving matrix in 1X TAE buffer may be used.

Other sieving matrices may be used within the practice of the present invention. High molecular weight linear polyacrylamide (LPA) with optimized concentration has pushed sequencing read-length to >1000 bases in 1 hr (Salas-Solano et al., 1998a, 1998b; Ruiz-Martinez et al., 1998).

Electrophoresis may be carried out under standard conditions, as disclosed by Liu et al. (1999). A detection system such as the laser confocal fluorescence detection system disclosed by Liu et al. (1999) may be used for one-color or four-color sequencing separations.

Raw DNA sequencing data traces may be reduced and base-called using the BaseFinder program according to Giddings et al. (1998). The data are first treated by baseline correction and then reduced by performing a multicomponent matrix transformation to correct for spectral cross-talk Liu et al. (1999). Data may be analyzed including primer peak deletion, baseline subtraction, spectral separation to remove cross-talk, several rounds of successive noise filtering and deconvolution, a final noise filtering, histogram equilization, mobility shift correction and base-calling Liu et al. (1999).

Bonding

Bonding-defects are generally caused by particles and chemical contaminants on the wafer surface. Various surface clean-up methods (pirahna etch, HF etch, Ammonia/$H_2O_2$, etc.) may be used for wafer cleaning. Stresses on the chip due to uneven temperature zones in the furnace during bonding should be minimized. Even temperature distribution in the furnace is highly desirable to achieve a zero dead volume chip injector.

Sample Preparation

A basic protocol was disclosed by Liu et al. (1999). Sequencing extension reactions may be produced using dideoxy nucleotides with cyanine-donor energy transfer dye-labeled primers. Standard methods and materials disclosed by Liu et al. (1999) for Sanger dideoxy reactions may be used in the practice of the present invention. Such methods are non-limiting and are for illustrative purposes only. The skilled artisan will realize that a variety of sample preparation methods and apparatus known in the art may be used in the practice of the present invention.

Development of high-throughput and automated DNA sequencing instrumentation moves the throughput bottleneck to sample preparation. The basic approaches currently employed are represented by the various active genome centers. Multiplex sequencing is being developed and used by the Harvard and Collaborative Research groups (Church, 1994) and at Utah (Gesteland et al., 1995). Direct transposon strategies are being employed at LBL (Martin et al., 1994) and at a variety of other locations (Berg et al., 1994; Kasai et al., 1992).

Recent efforts have centered on the development of more convenient and more automated sample preparation procedures. Robotic workstations such as the ABI Catalyst 800 and the Biomek 1000 are being used to automate the preparation of sequencing reactions. In addition, robotic work systems have been developed which integrate and automate plaque picking and growth, M13 template purification, and the preparation of DNA sequencing reactions (Watson et al., 1993). The latter approach exploits magnetic bead template capture methods which permit the rapid purification of DNA without the need for complicated precipitation or centrifugation steps (Hawkins, 1992; Uhlen, 1993; Holmberg et al., 1994). Detailed protocols have been published for performing fluorescent chemistries for automated primer directed sequencing (Hawkins et al., 1992; Wilson et al., 1990) for rapid preparation of M13 template DNA (Wilson, 1993), and for performing transposon-facilitated DNA sequencing (Martin et al., 1994; Strathmann et al., 1991). In general, most of these automated sample preparation methods involve the robotic performance of exactly the operations that would be performed by a technician. While these sample preparation methods have greatly increased throughput, the cost of reagents still remains a major component of the cost of sequencing.

Minimizing reagent consumption is one way to reduce the sequencing cost. A capillary array instrument requires only subattomoles of sample for each separation. A normal preparation of approximately 10 $\mu$l of DNA sequencing solution contains orders of magnitude more than the required sample. Thus, the present invention should substantially reduce the sample preparation volume, and the associated cost of DNA sequencing.

Several groups are involved in developing techniques for increasing the throughput and reducing the reaction volume of DNA sequencing. Tan and Yeung (1998) have developed an eight-channel automated flow-through device using freeze-thaw valving to manipulate fluids and air-cycling in capillaries to amplify the DNA. Friedman and Meldrum (1998) have developed a capillary sample prep system that can process 1,000 samples every eight hours, allowing solutions to be automatically loaded, mixed, and individually cycled. For reduction in reaction volume, Culbertson et al., (1998) have described a technique for solid-phase cycle sequencing in 64 nl capillaries directly coupled to a CE instrument. Any of the methods and apparatus disclosed above, or their equivalents, may be used in conjunction with the hybrid chip injector and capillary array within the scope of the present invention.

Sequencing on a Single Microfabricated CE Channel

A microfabricated chip injector for DNA sequence analysis was used by Liu et al., (1999). Separations were performed on a 7-cm-long microfabricated electrophoresis channel (Liu et al., 1999). One-color sequencing separation was extended to ~700 bases, and 502 bases were sequenced with single base resolution (>0.5) in 9.2 min (Liu et al., 1999). A four-color separation of an M13 sequencing sample on a 6.5-cm-long channel also was presented (Liu et al., 1999). The separation time for a sequence of about 600 bases was around 20 min (Liu et al., 1999). Base-calling accuracy reached 100% up to 450 bases, and 99.4% up to 500 bases (Liu et al., 1999). Sequencing on a single channel demonstrated high speed and reasonable resolution, but not high throughput. The hybrid apparatus of the present invention resolves the throughput issue by providing multiple electrophoresis channels in the form of a capillary array.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Microfabrication of Glass Chips

A schematic diagram showing a preferred embodiment of the hybrid apparatus of the present invention is provided in FIG. 1. A variety of methods known in the art may be used to make and use the claimed hybrid apparatus. For example, although the methods of Liu et al. (1999) were used to construct an electrophoretic chip, not the hybrid apparatus of the present invention, the disclosed chip microfabrication protocols or their equivalents known in the art may readily be adapted to produce the chip component of the hybrid apparatus of the present invention.

Alternative methods known in the art may be employed within the scope of the present invention. For example, for photolithograpy a thin sacrificial layer of Cr/Au may be deposited, followed by photoresist coating (Fan and Harrison, 1994). After soft baking, the photoresist may be exposed to UV radiation through a mask. The mask pattern will be transferred to the wafer after the photoresist is developed. After the exposed Cr/Au is etched off using gold and chromium etchants, the channel pattern is chemically etched into the glass. Then the residual photoresist and Cr/Au may be stripped and access holes were drilled. The etched wafer may be thermally bonded with another wafer.

Masks

Figure 9:
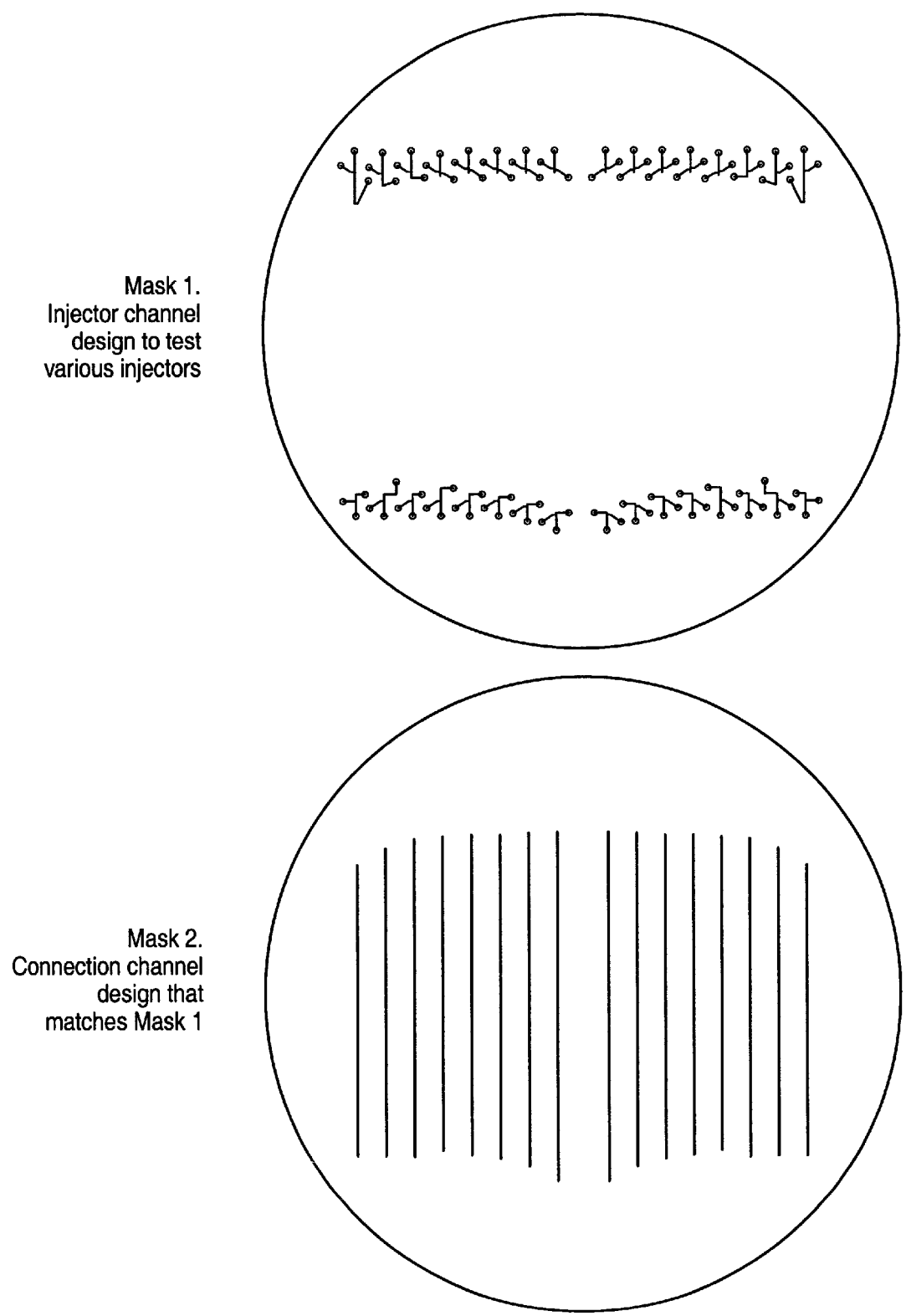
FIG. 9. Two mask process for chip injector.

In one embodiment of the present invention, a two-mask procedure is used to make the chip injector portion of the apparatus (see FIG. 9). The masks are generated with very fine lines ($\leq 10$ μm) and the line patterns are symmetric from one side to the other. The first mask (FIG. 9, top) is used to fabricate the injector array. The etching conditions are selected to form grooves with a depth that is slightly smaller than, or preferably precisely matches the inner radius of the array capillaries. The second mask (FIG. 9, bottom) is used to fabricate the connection channels. In this step, the etching conditions are selected to from grooves that are slightly greater than, or preferably precisely match the outer radius of the array capillaries. Due to isotropic etching, the formed groove has a profile very close to a semicircle. When two etched wafers are aligned and bonded, round channels are created. The resulting injector and connection channels respectively have diameters that match the i.d. and o.d. of the array capillaries. Consequently the assembly will have virtually no dead volumes for electrophoretic separation.

Figure 8:
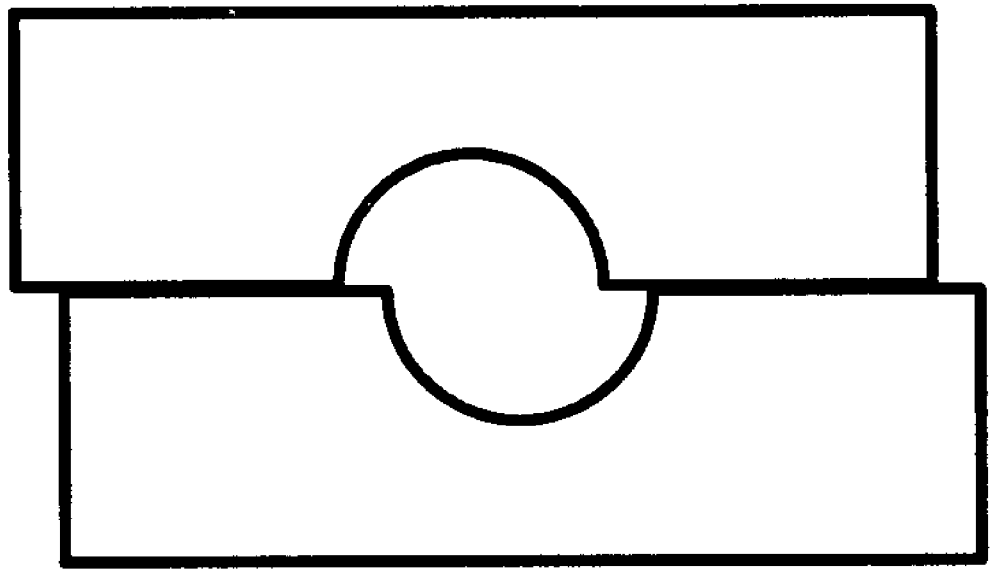
FIG. 8. Effect of channel alignment.

Proper alignment is extremely important to fabricate round channels. Cross section channels as shown in FIG. 8 may form due to poor alignment or shift of the wafers during bonding. The two-mask process described above allows alignment of two wafers within ±10 μm. The reason for this poor alignment is due to blurry outline of the alignment markers after etching. When channels are etched, the alignment markers will be etched as well. The line width of the markers changes to ~100 μm (the same width as the cross channels) or ~200 μm (the same width as the connection channels). These fat alignment markers make it difficult to align two wafers with good accuracy and precision.

Figure 7:
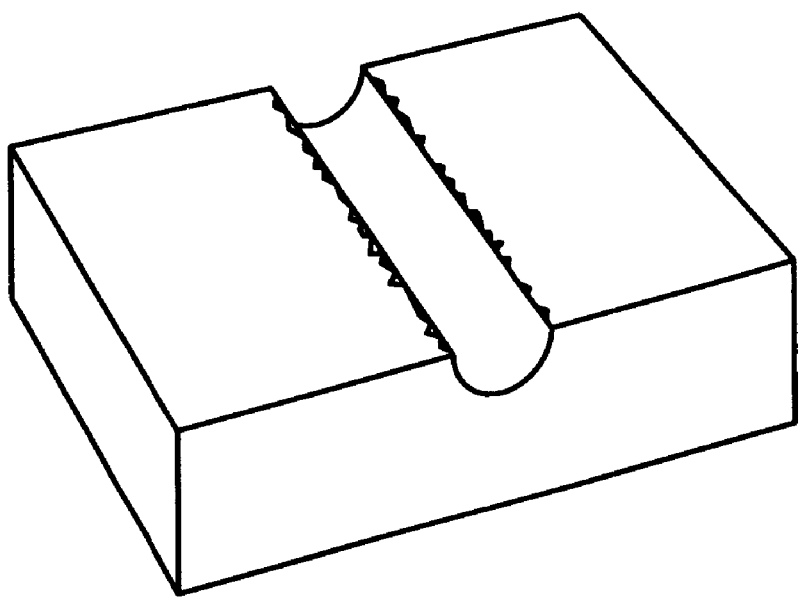
FIG. 7. Channels of rough and flat boundaries.
Figure 7:
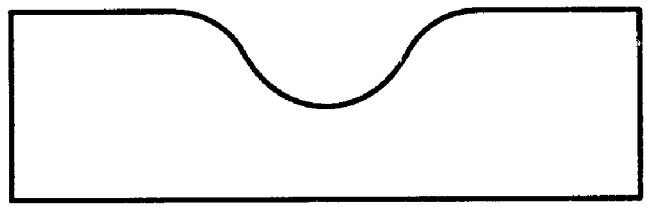
Figure 10:
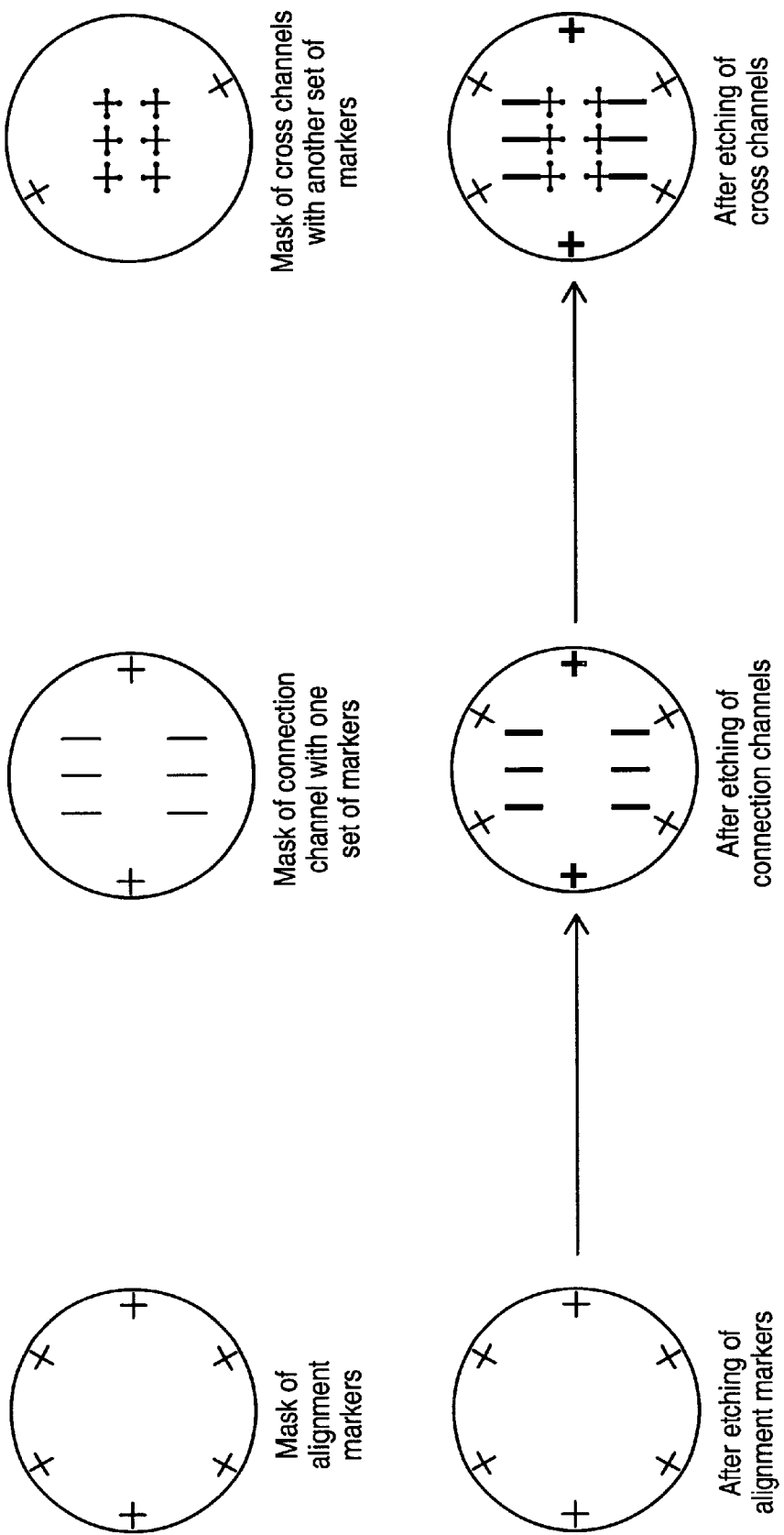
FIG. 10. Three mask process for chip injector.
Figure 11:
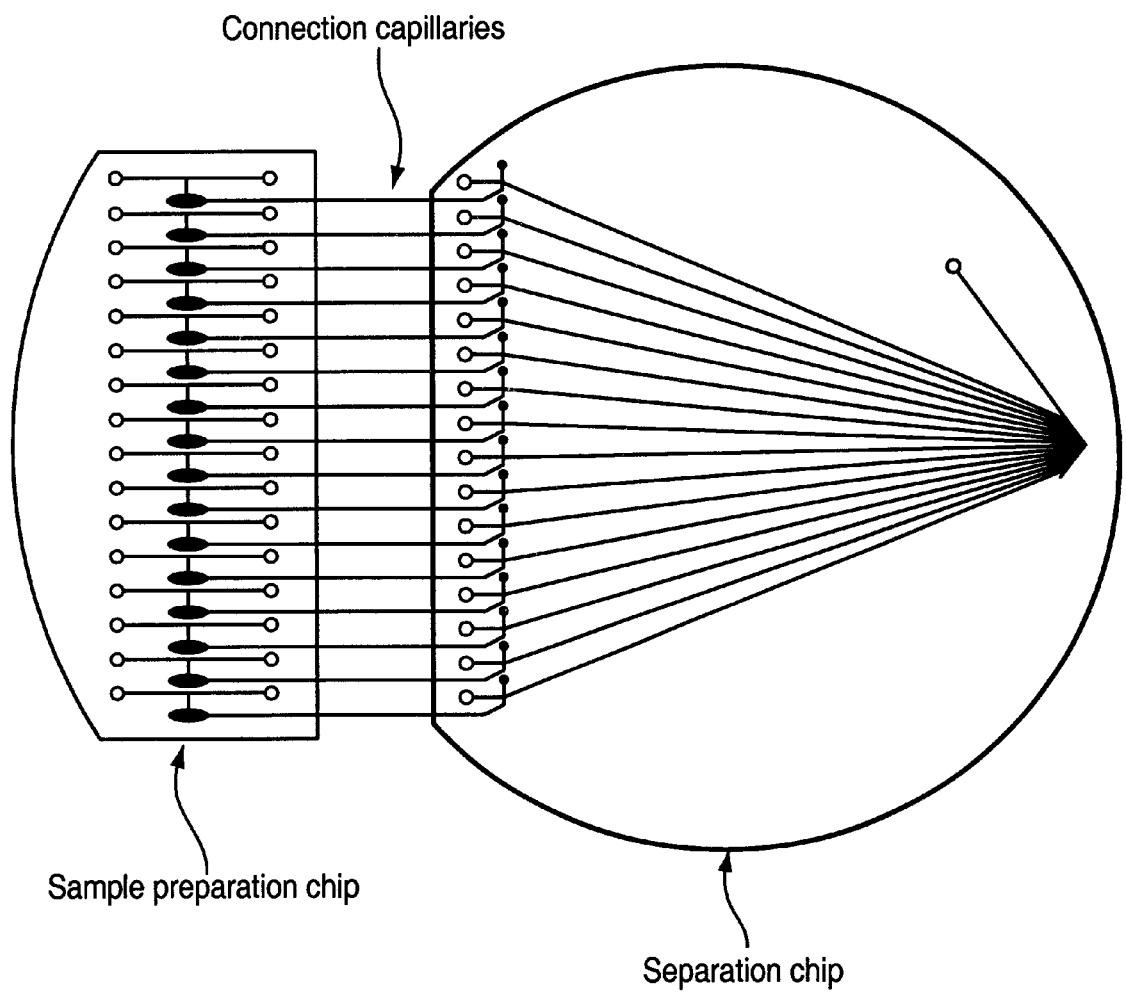
FIG. 11. An example of chip to chip communication via capillaries.

A three-mask process (FIG. 10) may be used to improve the alignment accuracy. The first mask is used to make the alignment markers only. This mask will consist of three sets of markers, one for the connection channels, one for injector and cross channels, and the third one for bonding alignment. As illustrated in FIG. 7, three sets of markers will be pre-etched onto the wafer-to-be-used, with a channel width of $\leq 10$ μm. With this approach, the alignment accuracy will be substantially improved.

Reduction and Elimination of Dead Volume

In preferred embodiments of the present invention, the dead volume of the hybrid apparatus is minimized or virtually eliminated. Dead volumes mainly come from three sources:

(see FIG. 1), (1) mismatch between i.d. of connection channels and o.d. of the array capillaries, (2) mismatch between i.d. of injector and cross channels and i.d. of the array capillaries, and (3) mismatch at the joint.

Figure 5:
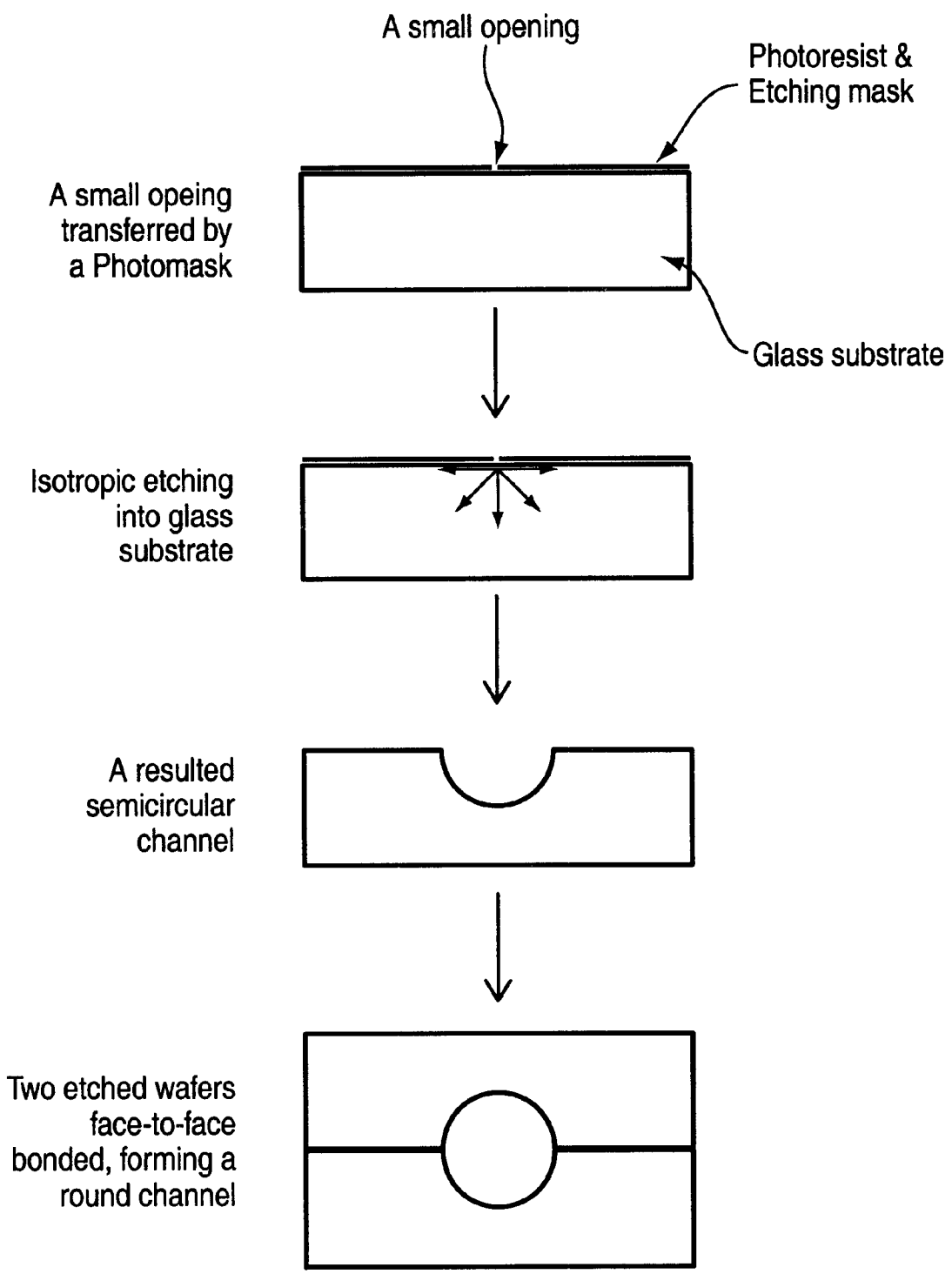
FIG. 5. Formation of a round channel by isotropic etching and bonding of two etched wafers.

When wet-etch using hydrofluoric acid is used for glass wafer etching, a characteristic of this etching process is that it is isotropic. Starting with a very narrow line opening (the line width of the mask pattern), isotropic etching results in a semicircular channel as shown in FIG. 5. For example, if the line width of the photomask is 5 μm, a 100-μm-deep channel is very close to a semicircle with a long radius of 102.5 μm and a short radius of 100 μm. A very "round" channel is formed after two etched wafers are face-to-face aligned and bonded. The dead volume is very small when a 200-μm-o.d. capillary is inserted into such a "round" channel. In practice, the polyimide coating on the capillary helps to further minimize the dead volume. Generally, more polyimide coating is scratched off on the short radius side than on the long radius side. The capillary may be coated with some soft material (e.g. wax) to further reduce or even eliminate this dead volume.

To minimize the second dead volume, a two-mask process is used to fabricate semicircular channels having different radius (depth). The wider connection channels are etched first using one mask and then the narrower injector and cross channels are fabricated using a different mask. A chip-injector is produced after aligning and bonding of the two etched wafers, as schematically illustrated in FIG. 1. In alternative embodiments, use of a three-mask process results in an apparatus with even lower dead volume.

Figure 6:
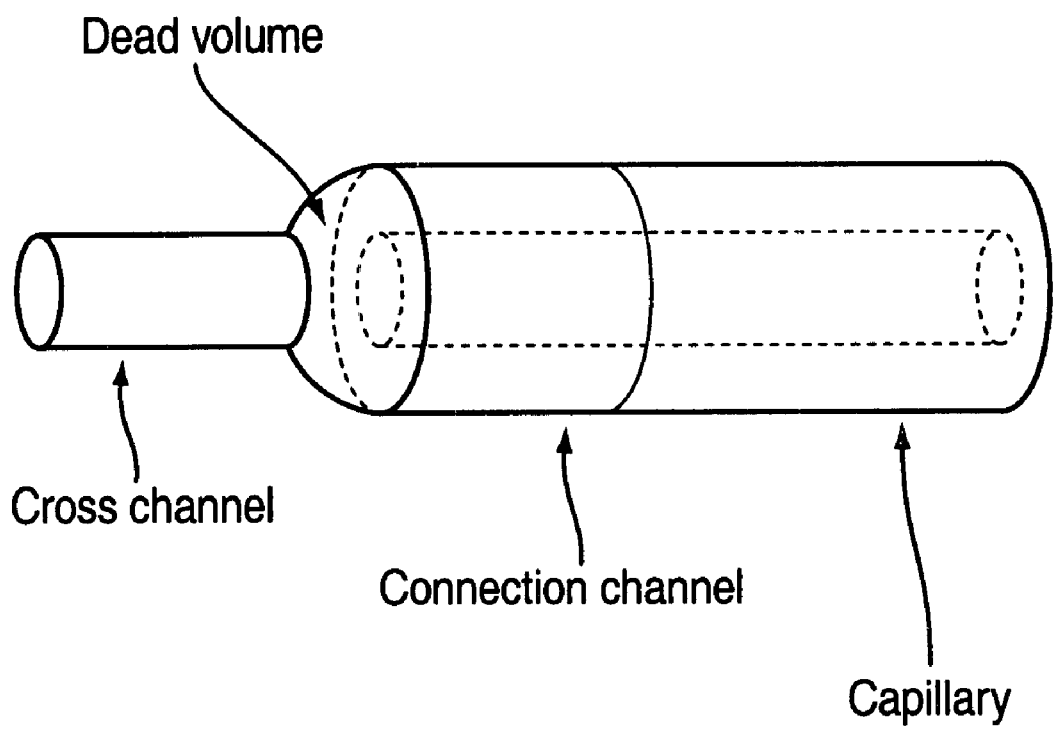
FIG. 6. Effect of joint mismatch on dead volume.

Isotropic etching makes round-ended channels. When a flat-ended capillary is joined with the microfabricated channel, a dead-volume is created (see FIG. 6). This dead-volume is generally small (<2 nl). The flat end of the capillary may be ground or a molded plastic injector that has a flat-ended channel may be used so as to minimize the dead-volume.

In preferred embodiments, the hybrid apparatus injector chip and capillary array may be incorporated into a fully automated system for DNA sequencing. The automated process may include loading samples, moving and aligning the chip relative to a fluorescence or other detector, moving sample to the injector electrokinetically using, for example, a pinched-injection mode, separating the fragments electrophoretically, presenting the used chip for replacement, and finally washing the electrodes for the next assay. Total assay time would be substantially less than one hour. Depending upon the length of the capillaries and other conditions, run times of may be achieved of 10 minutes or less.

All of the COMPOSITIONS, METHODS and APPARATUS disclosed and claimed herein can be made and executed without undue experimentation in light of the present disclosure. While the compositions and methods of this invention have been described in terms of preferred embodiments, it will be apparent to those of skill in the art that variations may be applied to the COMPOSITIONS, METHODS and APPARATUS and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Ansorge et al., Automated DNA Sequencing: Ultrasensitive Detection of Fluorescent Bands during Electrophoresis. *Nucleic Acids Research* 15:4593, 1987.

Berg et al.,. Transposon-Facilitated Sequencing. In *Automated DNA Sequencing and Analysis*. Edited by Adams, M. D.; Fields, C.; and Venter, J. C. pp. 51–59, Academic Press, San Diego, Calif., 1994.

Best et al., Separation of Fragments up to 570 Bases in Length by Use of 6-Percent T Non-Cross-Linked Polyacrylamide for DNA Sequencing in Capillary Electrophoresis. *Anal Chem.* 66:4063–7, 1994.

Carrilho et al., *Anal. Chem* 68:3305–13, 1996.
Church, G. M. Automated Multiplex Sequencing. In *Automated DNA Sequencing and Analysis*. Edited by Adams, M. D.; Fields, C.; and Venter, J. C. pp. 11–15, Academic Press, San Diego, Calif. 1994.
Cohen et al., Separation and Analysis of DNA Sequence Reaction Products by Capillary Gel Electrophoresis. *J Chromatogr.* 516:49–60, 1990.
Culbertson et al., *Anal. Chem.*, 70:3781–3789, 1998.
Dovichi, N. J. *The International Society for Optical Engineering*-SPIE. Feb. 4–10, San Jose, Calif., 1995.
Drossman et al., High-Speed Separations of DNA Sequencing Reactions by Capillary Electrophoresis. *Anal Chem.* 62:900–3, 1990.
Effenhauser et al., *Anal. Chem.*, 66:2949–2953, 1994.
Fan and Harrison, *Anal. Chem.* 66:177–184, 1994.
Friedman, N. A. and Meldrum, D. R. Capillary Tube Resistive Thermal Cycling. *Anal. Chem*, 70:2997–3002, 1998.
Gesteland et al., An Integrated and Automated System for Large Scale DNA Sequencing. San Jose, Calif. *The International Society for Optical Engineering-SPIE*, 1995.
Giddings et al., *Genome Res.* 8:644–65, 1998.
Hawkins, T. M13 Single-Stranded Purification Using a Biotinylated Probe and Streptavidin Coated Magnetic Beads. *J. DNA Seq. and Mapping* 3:65–9, 1992.
Hawkins et al., Fluorescence Chemistries for Automated Primer-Directed DNA Sequencing. *Electrophoresis* 13:552–9, 1992.
Hjerten, *J. Chromatogr.* 347:191–98, 1985.
Holmberg et al., Automatic Preparation of DNA Templates for Sequencing on the ABI Catalyst Robotic Workstation. In *Automated DNA Sequencing and Analysis*. Edited by Adams, M. D.; Fields, C.; and Venter, J. C. pp. 139–45, Academic Press, San Diego, Calif., 1994.
Huang et al., Capillary Array Electrophoresis Using Laser-Excited Confocal Fluorescence Detection. *Anal. Chem.* 64:967–72, 1992a.
Huang et al., DNA Sequencing Using Capillary Array Electrophoresis. *Anal. Chem.* 64:2149–54, 1992b.
Hunkapiller et al., Large Scale and Automated DNA Sequence Determination. *Science* 254:59–67, 1991.
Jacobson and Ramsey, *Anal. Chem.*, 68:720–723, 1996.
Jacobson et al., *Anal. Chem.*, 66:1107–1113, 1994.
Kasai et al., Efficient Large Scale Sequencing of the *E. Coli Genome*: Implementation of a Transposon- and PCR-based Strategy for the Analysis of Ordered λ-phage clones. *Nucl. Acids Res.* 20:6509, 1992.
Liu et al., Optimization of high-speed DNA sequencing on microfabricated capillary electrophoresis channels. *Anal. Chem.* 71:566–573, 1999.
Luckey et al., High Speed DNA Sequencing by Capillary Electrophoresis. *Nucl. Acids Res.* 18:4417–21, 1990.
Luckey et al., *J Phys. Chem.* 97:3067–75, 1993.
Martin et al., Transposon-Facilitated Sequencing: An Effective Set of Procedures to Sequence DNA Fragments Smaller than 4 kb. In *Automated DNA Sequencing and Analysis*. Edited by Adams, M. D.; Fields, C.; and Venter, J. C. pp. 60–64, Academic Press, London, 1994.
Mathies, R. A. and Huang, X. C. Capillary Array Electrophoresis: An Approach to High-Speed, High-throughput DNA Sequencing. *Nature* (London) 359:167–9, 1992.
Mathies et al., Laser-Excited Confocal Fluorescence Gel Scanner. *Reviews of Scientific Instruments* 65:807–12, 1994.
Mathies et al., Microfabricated Capillary Array Electrophoresis Systems for High-Performance DNA Sequencing and Genotyping. HPCE'99 Final Program p41, 1999, Palm Spring, Calif.
Maxam, A. M.; Gilbert, W. A New Method for Sequencing DNA. *Proc. Natl. Acad. Sci. U.S.A.* 74:560–4, 1977.
McCormick et al., *Anal. Chem.* 69:2626–2630, 1997.
Muller et al., *Electrophoresis*, 19:1436–44, 1998.
Mullikin, J. C. and McMurray, A. A. Sequencing the Genome, Fast. *Science* 283:1867–8, 1999.
PCT Application No. WO 94/05414
Pennisi, E. Sequencer' Trial by Fire. *Science* 280:814–817, 1998.
Pennisi, E. Academic Sequencers Challenge Celera in a Sprint to Finish. *Science* 283:1822–3, 1999.
Prober et al., A System for Rapid DNA Sequencing with Fluorescent Chain-Terminating Dideoxynucleotides. *Science* 238:336–41, 1987.
Ruiz-Martinez et al., DNA Sequencing by Capillary Electrophoresis with Replaceable Linear Polyacrylamide and Laser-Induced Fluorescence Detection. *Anal. Chem.* 65:2851–8, 1993.
Ruiz-Martinez et al., *Anal. Chem.*, 70:1528–1535, 1998.
Salas-Solano et al, *Anal. Chem.*, 70:1528–1535, 1998a.
Salas-Solano et al., *Anal. Chem.*, 70:3996–4003, 1998b.
Sanger et al., DNA Sequencing with Chain Termination Inhibitors. *Proc. Natl. Acad. Sci. U.S.A.* 74:5463–7, 1977.
Schmalzing et al., DNA sequencing on microfabricated electrophoretic devices. *Anal. Chem.*, 70:2303–2310, 1998
Schmalzing et al., *Proc. Natl. Acad Sci U.S.A.* 94:10273–10278, 1997.
Shi, Y. et al., *Anal. Chem.* Accepted.
Simpson et al., *Proc. Natl. Acad Sci. U.S.A.*, 95:2256–2261, 1998.
Smith et al., Fluorescence Detection in Automated DNA Sequence Analysis. *Nature* 321:674–9, 1986.
Soper et al., DNA-sequencing Reactions Performed in a Solid-Phase Nanoreactor Directly Coupled to Capillary Gel Electrophoresis. *Anal. Chem.* 70:4036–43, 1998.
Strathmann et al., Transposon-Facilitated DNA Sequencing. *Proc. Natl. Acad. Sci. U.S.A.* 88:1247–50, 1991.
Swerdlow et al., Three DNA Sequencing Methods Using Capillary Gel Electrophoresis and Laser-Induced Fluorescence. *Anal. Chem.* 63:2835–41, 1991.
Swerdlow et al., *Anal. Chem.*, 69:848–855, 1997.
Tabor, S. and Richardson, C. C.; DNA Sequence Analysis with a Modified Bacteriophage T7 DNA Polymerase effect of Pyrophosphorolysis and Metal Ions. *J. Biol. Chem.* 265:8322–8, 1990.
Takahashi et al., Multiple Sheath-flow Gel Capillary Array Electrophoresis for Multicolor Fluorescent DNA Detection. *Anal. Chem.* 66:1021–6, 1994.
Tan, and Yeund, *Anal. Chem*, 69:664–674, 1997.
Tan, H. and Yeung, E. S. Automation and Integration of Multiplexed On-Line Sample Preparation with Capillary Electrophoresis for High-Throughput DNA Sequencing. *Anal. Chem.* 70:4044–53, 1998.
Ueno, K. and Yeung, E. S. Simultaneous Monitoring of DNA Fragments Separated by Electrophoresis in a Multiplexed Array of 100 Capillaries. *Anal. Chem.* 66:1424–31, 1994.
Uhlen, M. Magnetic Separation of DNA. *Nature* (London) 362:569–70, 1993.
U.S. Pat. No. 5,296,375
U.S. Pat. No. 5,304,487
U.S. Pat. No. 5,483,075
U.S. Pat. No. 5,856,174
U.S. Pat. No. 5,904,824
U.S. Pat. No. 5,906,723

U.S. Pat. No. 5,976,336
U.S. Pat. No. 5,958,203
U.S. Pat. No. 6,001,229
U.S. Pat. No. 6,042,709
U.S. Pat. No. 6,054,034
U.S. Pat. No. 6,046,056
Watson et al., The Caenorhabditis Elegans Genome Sequencing Project: First Steps in Automation. *Nature* (London) 362:569–70, 1993.
Wilson, R. K. High-Throughput Purification of M13 Templates for DNA Sequencing. *Biotech.* 15:414–22, 1993.
Wilson et al., Development of An Automated Procedure for Fluorescent DNA Sequencing. *Genomics* 6:626–34, 1990.
Wooley and Mathies, *Proc. Natl. Acad Sci. U.S.A.*, 91:11348–11352, 1994.
Wooley and Mathies, *Anal. Chem.*, 67:3676–3680, 1995.
Wooley et al., *Anal. Chem.*, 68:4081–4086, 1996.
Wooley et al., *Anal. Chem.*, 69:2181–2186, 1997.
Zhang et al., Microfabricated Devices for Capillary Electrophoresis-Electrospray Mass Spectrometry, *Anal. Chem.* 71: 3258–3264, 1999.

What is claimed:

1. A hybrid apparatus for high throughput, high resolution electrophoretic separation comprising a microfabricated chip injector attached to one or more capillaries, each capillary connected in a straight line with an injection channel in the chip injector.

2. The apparatus of claim 1, wherein the microfabricated chip injector comprises:

a) one or more connection channels that match the outside shape of the capillary; and b) one or more injector channels that match the inside shape of the capillary.

3. The apparatus of claim 2, wherein the capillary is inserted into the connection channel until the injection channel is flush with a channel inside the capillary, resulting in an assembly having minimal dead volume.

4. The apparatus of claim 3, wherein each injection channel is connected by a first cross channel to a sample reservoir, by a second cross channel to a waste reservoir, and by a third cross channel to a cathode reservoir.

5. The apparatus of claim 3, wherein the injection channel is smoothly connected to the e channel inside the capillary.

6. The apparatus of claim 3, wherein the apparatus comprises at least 10 capillaries.

7. The apparatus of claim 6, wherein the apparatus comprises at least 100 capillaries.

8. The apparatus of claim 7, wherein the apparatus comprises at least 200 capillaries.

9. The apparatus of claim 8, wherein the apparatus comprises at least 300 capillaries.

10. The apparatus of claim 9, wherein the apparatus comprises at least 400 capillaries.

11. The apparatus of claim 10, wherein the apparatus comprises at least 500 capillaries.

12. The apparatus of claim 11, wherein the apparatus comprises at least 700 capillaries.

13. The apparatus of claim 12, wherein the apparatus comprises at least 900 capillaries.

14. The apparatus of claim 3, wherein the apparatus is capable of performing DNA sequence analysis of at least 500 bases of DNA sequence.

15. The apparatus of claim 14, wherein the apparatus is capable of performing DNA sequence analysis of at least 800 bases of DNA sequence.

16. The apparatus of claim 15, wherein the apparatus is capable of performing DNA sequence analysis of between 800 and 1000 bases of DNA sequence.

17. The apparatus of claim 15, wherein the apparatus is capable of performing DNA sequence analysis of greater than 1000 bases of DNA sequence.

18. The apparatus of claim 3, wherein the apparatus is designed to operate with a sample volume of 5.0 $\mu$l or less.

19. The apparatus of claim 3, further comprising a rotary scanner.

20. A method of sequencing DNA, comprising:

a) performing a Sanger dideoxy reaction with a sample of DNA to be sequenced;

b) loading the products of said reaction into one or more sample reservoirs of the apparatus of claim 3;

c) performing an electrophoretic separation of said products;

d) detecting said separated products; and e) analyzing said detected products to provide DNA sequence data.

21. The method of claim 20, wherein said reaction products are fluorescently labeled.

22. The method of claim 21, further comprising four color DNA sequencing.

* * * * *